United States Patent
Heinrich et al.

(10) Patent No.: US 9,642,264 B2
(45) Date of Patent: May 2, 2017

(54) MEDICAL OR DENTAL HANDLE

(71) Applicant: W&H Dentalwerk Bürmoos GmbH, Bürmoos (AT)

(72) Inventors: Christoph Heinrich, Salzburg (AT); Hannes Wagner, Salzburg (AT); Karl Schmiedlechner, Ostermiething (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 51 days.

(21) Appl. No.: 13/928,207

(22) Filed: Jun. 26, 2013

(65) Prior Publication Data

US 2013/0343011 A1    Dec. 26, 2013

(30) Foreign Application Priority Data

Jun. 26, 2012 (EP) .................................... 12173500

(51) Int. Cl.
| | |
|---|---|
| *H05K 5/00* | (2006.01) |
| *A61C 1/00* | (2006.01) |
| *A61C 1/08* | (2006.01) |
| *A61C 1/12* | (2006.01) |

(52) U.S. Cl.
CPC ............ *H05K 5/0026* (2013.01); *A61C 1/00* (2013.01); *A61C 1/088* (2013.01); *A61C 1/12* (2013.01)

(58) Field of Classification Search
CPC ....... A61C 19/004; A61C 1/185; A61C 1/196; A61C 1/188
USPC ............................................ 433/29, 125–131
See application file for complete search history.

(56) References Cited

U.S. PATENT DOCUMENTS

| | | | | |
|---|---|---|---|---|
| 5,908,295 | A  * | 6/1999  | Kawata .................. | A61C 1/088 433/132 |
| 6,015,290 | A  * | 1/2000  | Rosenstatter .......... | A61C 1/088 433/29 |
| 9,521,745 | B2 * | 12/2016 | Fujimura ............. | G11B 5/4846 |
| 2004/0166464 | A1* | 8/2004  | Schneider ....................... | 433/29 |
| 2005/0271997 | A1* | 12/2005 | Mikami ............. | A46B 15/0002 433/29 |
| 2006/0183071 | A1* | 8/2006  | Hsuch ............................. | 433/29 |
| 2006/0215398 | A1* | 9/2006  | Farmer ..................... | G09F 9/33 362/227 |

(Continued)

FOREIGN PATENT DOCUMENTS

| | | |
|---|---|---|
| DE | 19702370 | 8/1997 |
| EP | 2420198 | 2/2012 |

OTHER PUBLICATIONS

Machine english translation of EP2420198.*
European Search Report for EP12173500 (mailed Nov. 26, 2012).

*Primary Examiner* — Yogesh Patel
(74) *Attorney, Agent, or Firm* — Klarquist Sparkman, LLP (57) ABSTRACT

A medical or dental handle for driving a medical instrument, comprises a housing with a drive device accommodated therein and/or a supply line for a drive device, a first connection device for detachably connecting a medical or dental instrument and a second connection device for detachably connecting the handle to a media source and/or a drive unit, at least one electric component preferably comprising a light-emitting diode, at least one electric contact and an electric connecting device, which connect electrically the at least one electric component and the at least one electric contact, wherein the electric connecting device comprises a flexible circuit board in the interior of the handle.

21 Claims, 4 Drawing Sheets

(56) References Cited

U.S. PATENT DOCUMENTS

| | | | |
|---|---|---|---|
| 2010/0243297 A1* | 9/2010 | Oosawa | G11B 5/486 174/251 |
| 2010/0279250 A1* | 11/2010 | Pond | A61C 1/0084 433/80 |
| 2011/0094790 A1* | 4/2011 | Lin | H05K 1/028 174/350 |
| 2012/0115101 A1* | 5/2012 | Rauchenzauner | A61C 1/05 433/29 |
| 2015/0297069 A1* | 10/2015 | Coppersmith | F21V 29/70 600/132 |

* cited by examiner

MEDICAL OR DENTAL HANDLE

CROSS REFERENCE TO RELATED APPLICATION

The present application claims priority from pending European Patent Application No. 12173500.5 filed Jun. 26, 2012, which is incorporated herein by reference.

FIELD

The present invention relates to a medical or dental handle for driving an instrument.

BACKGROUND

Medical or dental handles serve to drive medical instruments. Therefore the handles have a drive mechanism or a supply line for the drive mechanism. The handles themselves are preferably designed as handpieces or angle pieces having a first connecting device for connecting the medical or dental instruments, which preferably serve to process hard or soft tissue or for inserting implants. The handles may in particular be designed to be straight, curved or gun-shaped as well as being designed as parts of handpieces or angle pieces. To drive the medical instruments connected to the handles, the handles in particular, the drive devices or supply lines arranged therein can be connected to medical or dental units, motors or media sources by means of a second connection device, preferably by means of supply tubing. The dental units supply the working media required for the medical instruments and handles, for example, spray air and/or spray water for cooling and/or electric energy for supplying electric components arranged in the handles, e.g., one or more light-emitting diodes for illuminating the treatment sites, sensors or electric memories for storing preferably instrument-related data. For transmission of data and/or energy, the handles have electric contacts, preferably in the area of the connection devices.

It is known in the state of the art that the supply of electric energy to the electric components, in particular the at least one light-emitting diode takes place by means of electric lines in the handles extending from the at least one light-emitting diode through the handles up to the connection devices for connecting the handles to the supply tubing. In addition it is known that in addition to the at least one light-emitting diode additional electric components, e.g., an electronic power supply unit may be supplied with energy over electric lines. In the area of the connection devices for the supply tubing, the electric lines end in electric contacts, which can be detachably connected to contacts on the supply tubing. The ends of the electric lines facing the electric components can be connected to contacts on the electric components, in particular the at least one light-emitting diode and/or electronic power supply unit.

It is common in the state of the art to use electric cables as the electric lines for transmitting electric energy and/or data between the electric components and the electric contacts. The electric cables each have an electric conductor surrounded by an insulating material. In addition it is known that flat ribbon cables may be arranged in the handles to supply energy and/or data to multiple electric components. These ribbon cables have a plurality of electric conductors, which are arranged parallel to one another and each of which is surrounded by insulating material.

Finally to protect the electric components and the electric lines in particular the connections of the two components in the handles from dirt and moisture, at least the connections between the electric lines and the electric components are surrounded additionally with a further insulation material.

One disadvantage of this design of the energy and/or data transmission in the medical or dental handles by means of electric cables has proven to be the space required for the electric lines in the handles. Several electric cables for transmission of energy and/or data are necessary due to the arrangement of one or more electric components in the handles. These cables must be accommodated in the handles in addition to the drive devices or supply lines for the drive devices and the electric components and contacts. This is in conflict with a user-friendly design of the handles, in particular the smallest possible shape of the handles to improve handling for users.

Another disadvantage of the embodiment known in the state of the art is the connection of the electric components and the electric contacts to the electric cables. When using electric cables for transmission of energy and/or data, each of these connections must be created manually. It is common for the electric cables to be connected to the electric contacts, in particular the electric components, by means of a soldering method, where the solder serves as a physically bonded connection. Since the soldering operation is performed manually, it is extremely time-consuming and thus the connection of the electric components to the electric cables is associated with high costs.

In addition when using electric cables as the electric conductors, insulation of the connections, in particular the uninsulated ends of the electric cables which can be connected to the electric contacts of the electric components is necessary to protect them from mutual contact, soiling and moisture. This additional processing step is also associated with costs.

SUMMARY

One goal is to create a medical or dental handle which avoids the disadvantages of the state of the art while being simple to manufacture and making it possible to arrange the electric components and contacts of the handle in electric connection to one another in the handle in a simple and space-saving manner.

According to one exemplary embodiment of a medical or dental handle for driving a medical instrument, it has a housing with a drive device accommodated in it and/or a supply line for a drive device, a first connection device for connecting, in particular detachably, a medical in particular dental, instrument and a second connecting device for connecting, in particular releasably the handle to a media source and/or to a drive unit, at least one electric component, preferably comprising a light-emitting diode, at least one electric contact and one electric connecting device connecting the at least one electric component and the at least one electric contact to one another electrically, the electric connecting device comprising a flexible circuit board arranged inside the handle.

The flexible circuit board is formed by an insulating base body which is coated on one side or both sides with electrically conductive printed conductors, preferably made of copper, aluminum, nickel or an alloy. The base body itself is formed by a flexible carrier material, in particular a carrier film made of plastic. In addition to the preferably gold-plated printed conductors, the carrier has terminals, in particular solder pads to receive and contact the electric components which are electrically connected to printed conductors. The printed conductors are preferably protected from dirt and moisture by a cover layer and/or an insulation layer. This layer preferably comprises a paint, a film or an injection-molding component.

In addition, the flexible circuit board may have areas of differing flexibility. These are preferably formed by carrier layers and/or top layers and/or insulating layers of varying thickness. It is also conceivable for the carrier layer and/or the top layer and/or the insulating layer to be made of different materials having different bending properties.

In addition to the flexible circuit board, the electric connecting device preferably also includes a rigid circuit board with a rigid carrier material, such that the flexible and/or rigid circuit board has terminals for fastening the at least one electric component and/or the at least one electric contact. The two circuit boards of the electric connecting device are in particular electrically and mechanically connected to one another for transmitting the data and/or energy between the electric components.

Sections of the flexible and/or rigid circuit board are preferably arranged at different angles in the handle, preferably between 0 and 90 degrees to the longitudinal axis of the handle, so that they can be accommodated in a space-saving manner in the handle between the housing and the drive device. To do so, the flexible and/or rigid circuit board additionally preferably has a recess through which the drive mechanism, the supply line and/or at least one of the connection devices extends.

In addition, the electric connecting device is preferably detachably connected to the handle so that it is replaceable. Therefore the handle and/or the flexible and/or rigid circuit board has/have holding means, in particular a clamping connection for detachably connecting the electric connecting device to the handle.

According to a first exemplary embodiment of the handle for a medical or dental handpiece or angle piece having a tool receptacle preferably rotatably mounted, for a treatment tool and an electric connecting device according to one of the embodiments mentioned above, the flexible and/or rigid circuit board has two electrically insulated sections, such that an electric contact is provided on each of the two sections to arrange the electric contacts so that they are electrically insulated from one another on the flexible or rigid circuit board.

According to a second exemplary embodiment of the handle, in particular for a medical or dental coupling device for connecting a medical handpiece or angle piece to a supply tubing, the first and/or second connection device is/are formed as a coupling protrusion with a lateral surface, an end surface and a coupling base.

The section of the electric connecting device designed to receive the electric component or electric contact, in particular the rigid and/or flexible circuit board is preferably arranged in the coupling protrusion and/or in front of or behind the coupling base so that the at least one side of the flexible and/or rigid circuit board coated with electrically conductive printed conductors is facing the lateral surface or end face of the coupling protrusion or the preferably ring-shaped coupling base.

The least one electric component of the medical or dental coupling device preferably has at least one generator for converting mechanical energy into electric energy.

According to a third exemplary embodiment of the handle for a medical or dental drive unit which is arranged in the handle preferably includes an electric motor or an air motor for driving a medical or dental handpiece or angle piece connected to the drive unit, the electric connecting device of the handle is in particular the flexible and/or rigid circuit board, and the electric component in the housing is at least partially embedded in a sheathing material, in particular in a casting compound body or a paint layer.

In addition the first or second connection device of the handle of the drive device is preferably designed as a coupling recess having a lateral surface surrounding the recess and having an end surface such that the section of the electric connecting device which is designed for receiving the electric component or electric contact, in particular the flexible and/or rigid circuit board, is arranged in the housing of the handle between the lateral surface and the housing and/or behind the end face of the recess. The at least one side of the flexible and/or rigid circuit board coated with electrically conductive printed conductors is preferably facing the lateral surface or the end face of the coupling recess.

The present handle is characterized by the following advantages.

The possibility of a user-friendly design of the handles is one advantage of the invention. Due to the design of the inventive handle with an electric connecting device having a flexible circuit board, the electric components and contacts can be arranged in electric connection to one another in the handle, in particular between the drive device or the supply line for the drive device and the housing of the handle. This permits optimization of the size of the handle, in particular its housing so that handling is improved for the user.

In addition, the handle, in particular the electric connecting device having the flexible circuit board permits a simplified electric connection of the electric components and contacts in the handle. The electric components can be mounted on the circuit board automatically, in particular mechanically and electrically, preferably by means of automatic assembly equipment.

Another advantage in using a flexible circuit board for electric connection of the electric components and contacts consists of the fact that no additional insulation of the connecting points between the electric components and the electric lines, in particular the electric cables is necessary. The electric components and contacts can be arranged directly on the terminals, in particular on the soldered pads of the circuit board, in particular being soldered there, these terminals being an electric connection with the insulated printed conductors on the flexible circuit board. In this way the connection point does not have any free locations which must be protected from soiling and moisture.

The present invention is explained in greater detail below on the basis of several exemplary embodiments and in conjunction with the drawings.

DETAILED DESCRIPTION

Figure 1A:
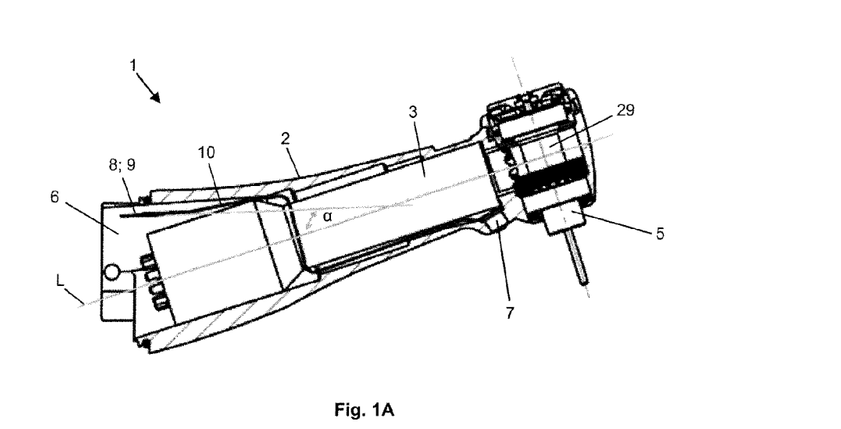
FIG. 1A shows a first exemplary embodiment of the handle for a preferably electrically operated medical or dental angle piece.

FIG. 1A shows a sectional diagram of a first exemplary embodiment of the handle 1 for a medical or dental angle piece, which is preferably operated electrically. For connection, in particular detachably, of a medical or dental instrument to the drive device 3 arranged in the handle 1, a first connection device 5 is preferably designed as a rotatably mounted tool receptacle 29. The drive device 29 itself preferably has a drive shaft which is rotatably mounted in the housing 2 of the handle 1 by means of at least one bearing. The housing 2 of the handle 1 is in turn preferably designed in a sleeve shape. For connection, in particular detachable, of the handle 1 to a media source and/or a drive unit, the handle 1 has a second connection device 6, which is preferably arranged at an angle to the first connection device 5. In addition to the drive device 3, preferably an electric component 7 comprising a light-emitting diode is arranged in the handle 1, in particular in the area of the first connection device 5. To supply the component 7 with electric energy, the handle has at least one electric contact 8, 9, which is preferably arranged in the area of the second connection device 6, which can in turn be connected to a media source and/or a drive unit. Finally, to electrically connect the electric component 7 and the at least one electric contact to one another, the handle 1 has an electric connecting device 10 which extends preferably from the first connection device 5 in the direction of the second connection device 6 to transmit data and/or energy. To accommodate the connecting device 10 in the handle 1, in particular between the housing 2 and the drive device 3 in a space-saving manner, it has sections which are arranged at different angles α in the handle, preferably between 0 and 90 degrees to the longitudinal axis of the handle.

Figure 1B:
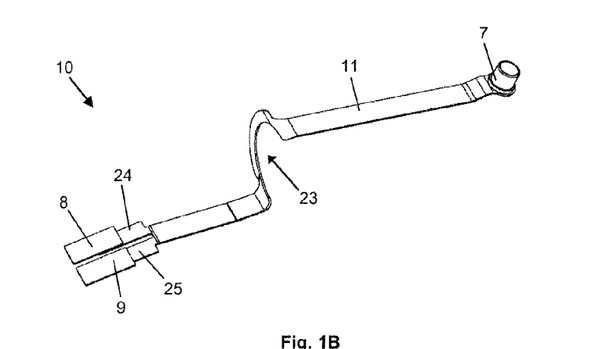
FIG. 1B shows the electric connecting device from FIG. 1A according to the first exemplary embodiment of the handle.

FIG. 1B shows the electric connecting device 10 from FIG. 1A arranged in the interior of the handle 1. The connecting device 10 comprises a flexible circuit board 11. The flexible circuit board 11 in this exemplary embodiment has at least two strip-shaped sections and one ring-segment-shaped section. The sections are preferably arranged at an angle to one another. The at least one ring-segment-shaped section surrounds a recess 23 which serves to arrange the flexible circuit board 11 in the handle 1 between the drive device 3, in particular the shaft arrangement and the housing 2. In addition to the strip-shaped segments and the ring-segment-shaped segment, the flexible circuit board 1 additionally has two sections 24 and 25 which are electrically insulated from one another, each of the two sections 24 and 25 being assembled with an electric contact 8 and 9. Due to the assembly of the circuit board 11, there is an electric connection of the contacts 8, 9 with the printed conductors arranged on the circuit board 11, so that data and/or energy may be transmitted to the circuit board 11. The flexible circuit board 11 is assembled with an electric component 7, in particular with a light-emitting diode on a second end. This light-emitting diode is in turn also electrically connected to the printed conductors of the circuit board 11 through the assembly. Due to the arrangement of the circuit board 11 in the handle 1, it is thus possible to transfer electric energy from the first connection device to the second connection device, in particular from the one end and/or the circuit board 11 having the electric contacts 8, 9 to the second end having at least one light-emitting diode 7.

Figure 1C:
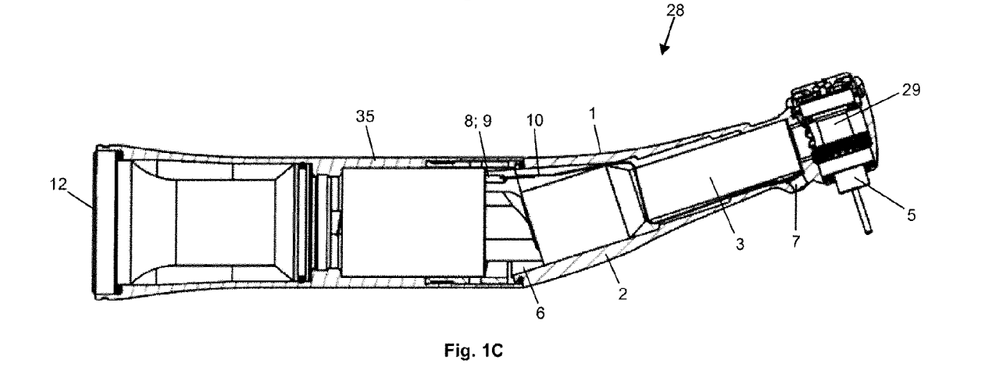
FIG. 1C shows a medical or dental angle piece having a handle according to FIG. 1A.

FIG. 1C shows a medical or dental angle piece 28 having a handle 1 according to FIG. 1A. The housing 2 of the angle piece 28 is designed in two parts. A connection piece 35 having a third connection device 12 for connection, in particular releasable connection, to a supply tubing (not shown) for connecting the angle piece 28 to a media source and/or to a drive unit is fixedly or detachably connected to the handle 1, in particular at its second connection device 6. The third connection device 12 is preferably arranged at an angle to the first and second connection devices 5, 6. The electric connecting device 10 with the electric contacts 8, 9 as well as the at least one electric component 7, in particular the light-emitting diode extends here from the first connection device to the second connection device at an angle to the longitudinal axis of the handle 1 between the housing 2 and the drive device 3. The electric contacts 8, 9 in the area of the second connection device 6, which are arranged on the connecting device 10, are preferably connected to additional electric contacts, in particular a generator, or electric lines, in particular electric cables, which are preferably arranged in the connection piece 35. These preferably extend to the third connection device 12. Alternatively, it is possible that the connecting device 10 extends from the first connection device 10 to the third connection device 12.

Figure 2A:
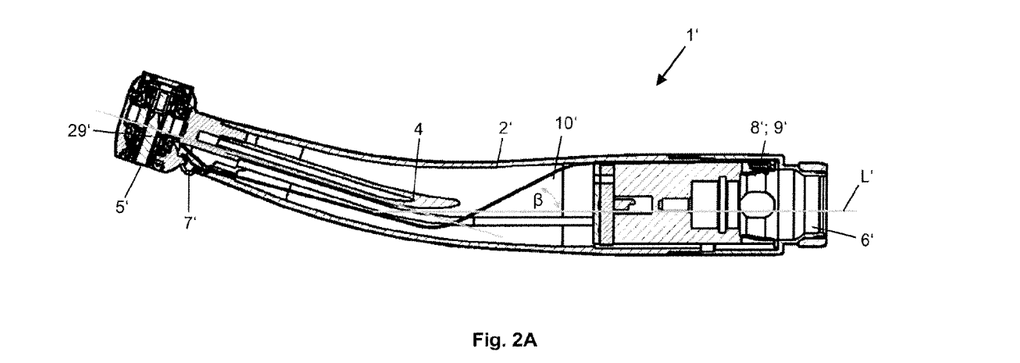
FIG. 2A shows a second exemplary embodiment of the handle for an air-operated medical or dental angle piece.

FIG. 2A shows a second exemplary embodiment of the handle 1' for an air-operated medical or dental angle piece, preferably a dental turbine. A supply line 4 for driving the tool receptacle 29' by means of a turbine rotor connected to the receptacle 29' is arranged in the housing 2' of the handle 1'. For connection, in particular releasable, of the handle 1' to a media source, in particular a supply tubing, the second connection device 6' has a coupling recess from which a second exemplary embodiment of the electric connecting device 10' extends in the direction of the first connection device 5', in particular in the direction of the tool receptacle 29' to electrically connect the electric contacts 8', 9' to the electric component 7', which preferably comprises a light-emitting diode. The first and second connection devices 5', 6' are arranged at an angle to one another in this exemplary embodiment. The electric connecting device 10' additionally has multiple sections which are arranged at different angles β, preferably between 0 and 90 degrees to the longitudinal axis L' in the handle 1' between the supply line 4 and the housing 2' to arrange the connecting device 10' in the housing 2' in a space-saving manner.

Figure 2B:
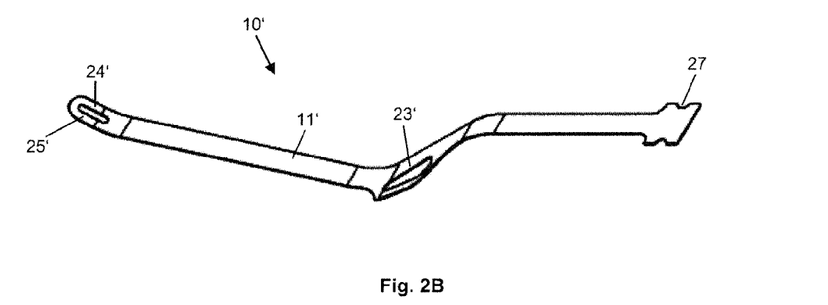
FIG. 2B shows the electric connecting device from FIG. 2A according to the second exemplary embodiment of the handle.

FIG. 2B shows the electric connecting device 10' from FIG. 2A according to the second exemplary embodiment of the handle 1'. The flexible circuit board 11' of the connecting device 10' has multiple sections designed essentially in strips as well as at least two ring-shaped sections. At least one of the ring-shaped sections surrounds a recess 23' through which the supply line 4 extends as shown in FIG. 2A. The other ring-shaped section of the electric connecting device 10' preferably has at least two sections 24', 25' that are electrically insulated from one another, one electric contact 8', 9' being arranged on each of the two sections 24', 25' as shown in FIG. 2A. Due to the arrangement of the two contacts 8', 9' at a distance from one another, in particular with insulation, on the circuit board 11', a possible electric contact, in particular an electric short circuit between the two contacts 8', 9' is prevented.

The electric connecting device 10' itself is preferably detachably connected to the handle 1'. To do so the connecting device 10' has holding means 27 for detachable connection to the handle 1'. The holding means 27 are preferably formed by grooves on the circuit board 11' and protrusions on the housing 2' of the handle 1'. This makes it possible to connect the electric connecting device 10' to the housing 2' of the handle 1' by a mechanical connection, e.g., a clamp connection. Alternatively it is also conceivable to form the connection of the two components by a screw connection, preferably by means of at least one additional recess in the circuit board 11', a recess with a thread on the housing 2' and with a screw.

Figure 3A:
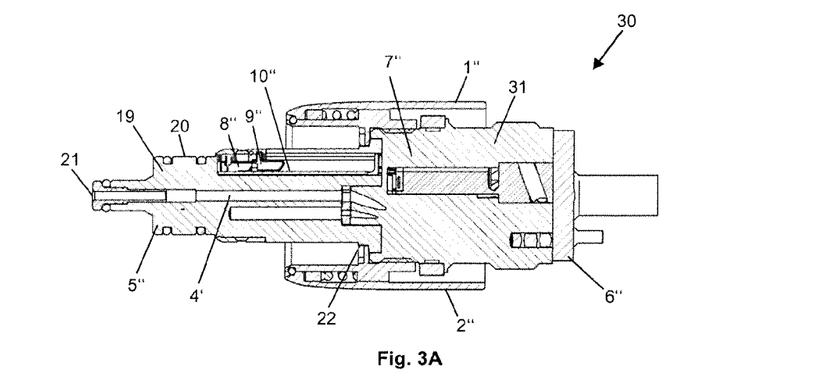
FIG. 3A shows a medical or dental coupling device having a third exemplary embodiment of the handle.

FIG. 3A shows a medical or dental coupling device 30 illustrated with a third exemplary embodiment of the handle 1". The coupling device 30 serves to connect a medical instrument, in particular a medical handpiece or angle piece to a media source and/or to a dental unit. To do so, the coupling device 30 has a first connection device 5" and a second connection device 6". At least one supply line 4' for supplying media to the instrument, for example, a working medium or a cooling medium is accommodated in the housing 2" of the coupling device 30. Furthermore, the coupling device 30 has an electric connecting device 10" having at least one electric component 7" as well as at least one electric contact 8", 9" such that the connecting device 10" electrically connects the two components 7"; 8', 9' to one another. The electric connecting device 10" is also arranged in the interior of the handle 1" in this exemplary embodiment and is designed as a flexible circuit board 11".

The electric component 7" preferably includes a generator 31 for converting mechanical energy into electric energy which can be transferred by means of the electric connecting device 10" from the coupling device 30, in particular via the first connection device 5" to the medical instrument connected to the coupling device 30. To do so the first connection device 5" is preferably designed as a coupling protrusion 19 with a lateral surface 20, an end face 21 and a coupling base 22, such that the section of the electric connecting device 10" formed to receive the electric contacts 8", 9" extends from the handle 1" into the coupling protrusion 19. The at least one side of the electric connecting device 10" which is coated with the electrically conductive printed conductors is preferably facing the lateral surface 20 of the coupling protrusion 19 so that the energy transfer between the coupling device 30 and the medical instrument can take place by way of the lateral surface 20 of the coupling protrusion 19. Alternatively, it is conceivable that the electric connecting device is arranged in front of or behind the coupling base 22, and the side of the electric connecting device 10" which is coated with the electrically conductive printed conductors faces the preferably ring-shaped coupling base 22. In addition, it is possible that the electric connecting device 10" also faces the end face 21 of the coupling protrusion 19.

Figure 3B:
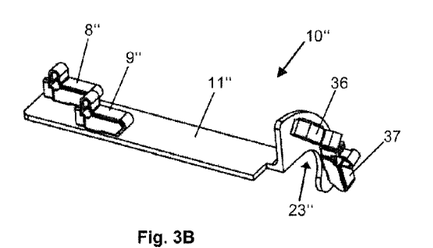
FIG. 3B shows the electric connecting device from FIG. 3A according to the third exemplary embodiment of the handle.

FIG. 3B shows the electric connecting device 10" from FIG. 3A, which has preferably two electric contacts 8", 9", preferably spring-mounted, as well as having two additional electric contacts 36, 37, in particular for detachable connection of the generator 31 to the electric connecting device 10" for energy transmission from the generator 31 to the medical instrument. The electric connecting device 10" is itself formed by a flexible circuit board 11", which is preferably formed by at least one strip-shaped section and at least one ring-segment-shaped section; which is arranged in the handle 1", preferably at an angle, especially at an angle of 90 degrees to the strip-shaped section of the circuit board 11" to form a recess 23" through which the at least one supply line 4' of the coupling device 30 extends.

Figure 4A:
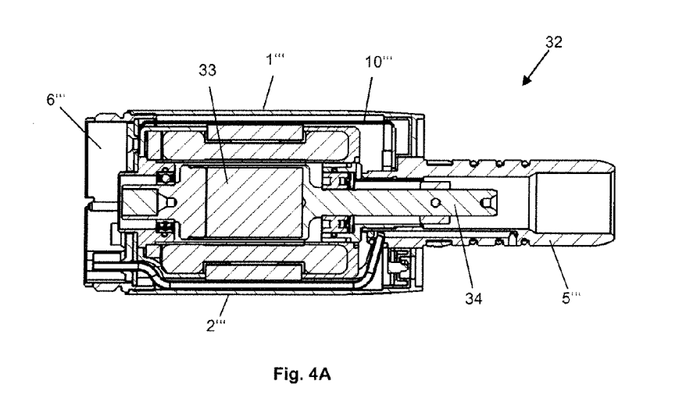
FIG. 4A shows a medical or dental drive unit having a fourth exemplary embodiment of the handle.

FIG. 4A shows a medical or dental drive unit 32 with a fourth exemplary embodiment of the handle 1'''. An electric motor 33 for driving a medical or dental handpiece or angle piece connectable to the drive unit 32 is arranged in the housing 2''' of the handle 1'''. The drive unit 32 has a drive shaft 34 in addition to the electric motor 33 to transmit a drive movement from the motor 33 to the handpiece or angle piece connectable to the handle 1'''. For connecting the handpiece or angle piece to the drive unit 32, in particular detachably, the latter has a first connection device 5'''. A second connection device 6''' serves for connection, in particular detachable, of the handle 1''' to a media source and/or to a dental unit. For transmission of data and/or energy between the two connection devices 5''', 6''', an electric connecting device 10' extends from the first connection device 5''' to the second connection device 6'. To do so, sections of the electric connecting device 10''' are arranged preferably at different angles in the handle 1''', especially between 0 and 90 degrees, in particular between the electric motor 33 and the housing 2''' of the drive unit 33.

Figure 4B:
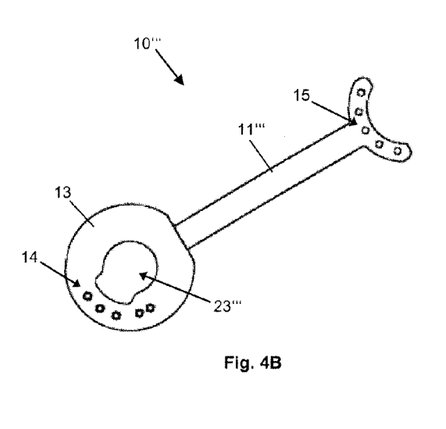
FIG. 4B shows the electric connecting device from FIG. 4A according to the fourth exemplary embodiment of the handle.

FIG. 4B shows an electric connecting device 10''' from FIG. 4A comprising in addition to the flexible circuit board 11' a rigid circuit board 13 such that the flexible circuit board 11''' has a flexible carrier material, preferably a carrier film and the rigid circuit board 13 has in particular a rigid carrier material. The two circuit boards 11''', 13 each have terminals 14, 15 for fastening and contacting the electric components, in particular the at least one electric component 7''' and the at least one electric contact 8''', 9'''. The terminals 14, 15 themselves are preferably formed by solder pads, which are electrically connected to the printed conductors of the electric connecting device 10'''. For space-saving arrangement of the electric connecting device 10''' in the handle 1''', it has a recess 23''' through which the drive shaft 34 of the drive unit 32 in particular extends.

Figure 4C:
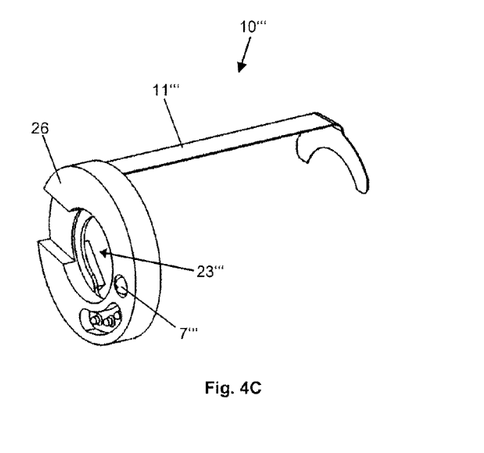
FIG. 4C shows the electric connecting device from FIG. 4B where the electric connecting device is preferably at least partially embedded in a sheathing material.

FIG. 4C shows the electric connecting device 10' from FIG. 4B, where the electric connecting device 10''' is at least partially embedded in a sheathing material 26. In particular the rigid circuit board 13 and the component 7''' comprising the electric light-emitting diode in the housing 1' are surrounded at least partially by the sheathing material 26 which is preferably made of a casting compound body. In addition to the rigid circuit board 13, the casting compound body 26 also has a recess 23'''. The flexible circuit board 11" of the electric connecting device 10''' extends from the rigid body 26, which is preferably arranged in the area of the first connection device 5''', to the second connection device 6''' of the handle 1'''.

The sheathing material 26, which is preferably made of a plastic is preferably applied by means of an injection molding or injection pressing process. Alternatively the sheathing material may also be formed by casting with or without a vacuum.

Figures 4D, 4E:
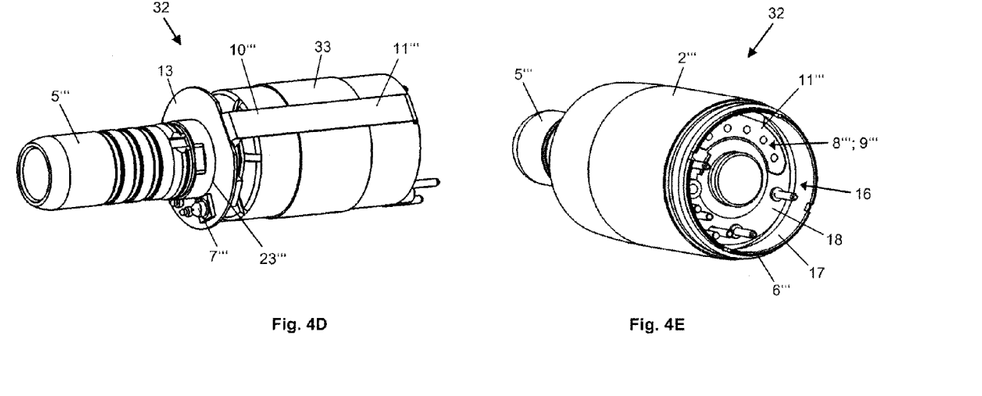
FIG. 4D shows the medical drive unit from FIG. 4A without the housing.
FIG. 4E shows also the medical drive unit from FIG. 4A without the housing but from the view of the second connecting device.

FIG. 4D shows the medical drive unit 32 from FIG. 4A without the housing 2''' and from the standpoint of the first connection device 5''' which is formed by a coupling protrusion. The rigid circuit board 13 of the electric connecting device 10' is arranged in front of the coupling base of the coupling protrusion in this exemplary embodiment and preferably extends radially to the longitudinal axis of the drive unit 32, in particular in the radial direction from the coupling protrusion, which is designed in particular in the form of a pin. To do so, the circuit board 13 has a recess 23'''. The at least one side of the rigid circuit board 13, which is coated with the electrically conductive printed conductors is preferably arranged in the direction of the end face of the coupling protrusion so that the at least one electric component 7', in particular the light-emitting diode points in the direction of the end face.

The flexible circuit board 11" of the electric connecting device 10''' extends in the axial direction along the electric motor 33 from the rigid circuit board 13, in particular from the first connection device 5''' formed by the coupling protrusion to the second connection device. The flexible circuit board 11' is therefore preferably arranged at approximately 90 degrees to the rigid circuit board 13. In the area of the second connection device the flexible circuit board 11' of the electric connecting device 10''' preferably has another section which is in turn arranged at an angle to the first section of the flexible circuit board 11'''. This serves to receive the at least one electric contact in the area of the second connection device.

FIG. 4E also shows the medical drive unit 32 with the first and second connection devices 5''', 6''' from FIG. 4A but with the housing 2''' and from the standpoint of the second connection device 6". The second connection device 6' is designed as a coupling recess 16 with a lateral surface 17 surrounding the recess and with an end face 18. The coupling recess 16 serves to receive an additional connection device, in particular a supply tubing for connecting the drive unit 32 to a media source and/or to a dental unit. The section of the electric connecting device 10''' designed to receive the at least one electric contact 8", 9", in particular the flexible circuit board 11' is therefore preferably arranged in the area of the second connection device 6''' in the housing 2''' of the handle 1' behind the end face 18 of the recess 16. The end face 18 is formed preferably by a cover (not shown), in particular a cover disk. The at least one side of the flexible circuit board 11" coated with electrically conductive printed conductors is preferably facing the end face 18, in particular the cover of the coupling recess 16, so that the at least one electric contact 8', 9''' arranged on the flexible circuit board 11' extends essentially parallel to the recess 16.

Within the scope of the present invention it is self-evident that the inventive medical or dental handle according to the invention is not limited to the exemplary embodiments described above and to the use in a medical or dental handpiece or angle piece, a coupling mechanism or a drive unit. The electric connecting device of the handle may be designed in particular to receive not only the at least one electric contact and the at least one electric component but also additional electric components, such as, for example, additional light-emitting diodes, sensors, electronic memories or electric switches. In particular the at least one electric contact, which is electrically connected via the electric connecting device, in particular by means of the flexible circuit board, to the at least one electric component, may be part of an additional electric component. Furthermore, the at least one electric contact and the at least one electric component may be arranged in the area of the first and/or second connection devices or in the interior of the handle, in particular at a distance from the first and/or second connection devices.

What is claimed is:

1. A medical or dental handle element for driving an instrument, comprising:
    a housing with a drive element accommodated therein and/or a supply line for a drive device,
    a first connection device at a first end of the housing for detachably connecting the instrument and a second connection device at a second end of the housing for detachably connecting the handle element to a media source and/or a drive unit,
    at least one electric contact positioned at or adjacent the first connection device or the second connection device, and
    an electric connecting device that electrically connects an electric component coupled or coupleable to the handle element and the at least one electric contact to transmit at least one of data and energy,
    wherein the electric connecting device comprises a flexible circuit board in the interior of the handle element with at least a first section extending longitudinally along the drive element and/or the supply line, and at least a second section extending transverse to an longitudinal axis of the drive element or the supply line, and
    wherein the second section forms a passage which partially surrounds at least one of the drive element or the supply line so that the at least one of the drive element or the supply line extends through the passage, or the second section forms a passage that surrounds at least one of the drive element or the supply line so that the at least one of the drive element or the supply line extends through the passage.

2. A medical or dental handle element according to claim 1, wherein the electric connecting device further comprises a rigid circuit board, and wherein the flexible circuit board comprises a flexible carrier material in the form of a carrier film, and the rigid circuit board comprises a rigid carrier material and wherein the rigid circuit board and the flexible circuit board are coupled to each other to form the electric connecting device.

3. A medical or dental handle element according to claim 2, wherein the rigid circuit board has terminals for attaching the at least one electric component or the at least one electric contacts.

4. A medical or dental handle element according to claim 2, wherein the electric component is disposed on the rigid circuit board and at least one of the electric component and the rigid circuit board is covered at least partially by a casting compound body or a paint layer.

5. A medical or dental handle element according to claim 1, wherein the flexible circuit board has first terminals for attaching the at least one electric component and/or at least one second terminal for connecting to the at least one electric contact.

6. A medical or dental handle element according to claim 1, the passage of the second section comprises at least one of a curved shape, a ring-segment shape, a circular shape and a ringed-shape.

7. A medical or dental handle element according to claim 1, wherein the flexible circuit board further comprises a recess defined at an end through which at least one of the connecting devices extends.

8. A medical or dental handle element according to claim 1, wherein the flexible circuit board has two sections, which are insulated electrically from one another, such that an electric contact is provided on each of the two sections.

9. A medical or dental handle element according to claim 1, comprising at least one of: a handpiece, a contra-angle handpiece, a medical or dental coupling device, a drive assembly having an electric motor or an air motor.

10. A medical or dental handle element according to claim 1, wherein the first connecting device comprises a tool receptacle for detachably holding an instrument.

11. A medical or dental handle element for driving an instrument, comprising:
   a housing with a drive element and/or a supply line for a drive device accommodated therein and having a longitudinal axis,
   a first connection device for detachably connecting the instrument and a second connection device for detachably connecting the handle element to a media source and/or a drive unit,
   electric contacts positioned adjacent the first or second connection device, and
   an electric connecting device that electrically connects an electric component coupled or coupleable to the handle element and the electric contacts for transmitting data and/or energy between the contacts and the electric component,
   wherein the electric connecting device comprises a flexible circuit board a portion of which comprises two sections which are electrically insulated from one another by a clearance between the two sections, wherein each of the two sections connects to one of the electric contacts and electrically insulates the electric contacts from each other through the clearance, and wherein the flexible circuit board forms a passage which partially surrounds at least one of the drive element or the supply line so that the at least one of the drive element or the supply line extends through the passage, or wherein the flexible circuit board forms a passage that surrounds at least one of the drive element or the supply line so that the at least one of the drive element or the supply line extends through the passage.

12. A medical or dental handle element for connecting to a handpiece or contra-angle handpiece, comprising:
   a housing with a drive device accommodated therein and/or a supply line for a drive device,
   a first connection device for detachably connecting to the handpiece or contra-angle handpiece and a second connection device for detachably connecting the handle element to a media source and/or a drive unit,
   electric contacts arranged at or adjacent the first or second connection device, and
   an electric connecting device that electrically connects an electric component coupled or coupleable to the handle element and the electric contacts for transmitting data and/or energy between the contacts and the electric component,
   wherein the electric connecting device comprises a flexible circuit board in the interior of the handle element with at least a first section and a second section, wherein the first section extends longitudinally along the drive element and/or the supply line and has a first end and a second end and wherein the second section is arranged at one of the first or second end, said second section extending transverse to a longitudinal axis of the drive element or the supply line and having a ring-segment shape or a ringed-shape, wherein said ring-segment shape or ringed-shape forms a passage through which at least one of the drive element, the supply line or a coupling pin of the medical or dental handle element extends.

13. A medical or dental handle element according to claim 12, wherein the flexible circuit board comprises a third section arranged at the other of the first or second end, said third section extending transverse to an longitudinal axis of the drive element or the supply line and having a ring-segment shape or a ringed-shape, wherein said ring-segment shape or ringed-shape forms a passage through which at least one of the drive element and the supply line or a coupling pin of the medical or dental handle element passes.

14. A medical or dental handle element according to claim 13, wherein the second section and the third section are substantially arranged in parallel to each other.

15. A medical or dental handle element according to claim 13, wherein at least one of the second section and the third section connects to the electric contacts arranged at or adjacent the first or second connection device.

16. A medical or dental handle element according to claim 13, wherein at least one of the second section and the third section comprises the electric component.

17. A medical or dental handle element according to claim 12, comprising at least one of: a medical or dental coupling device, a drive assembly having an electric motor or an air motor.

18. A medical or dental handle element for driving an instrument, comprising:
   a housing with a drive element accommodated therein and/or a supply line for a drive device,
   a first connection device at a first end of the housing for detachably connecting the instrument and a second connection device at a second end of the housing for detachably connecting the handle element to a media source and/or a drive unit,
   at least one electric contact positioned adjacent the first connection device or the second connection device, and
   an electric connecting device that electrically connects an electric component coupled or coupleable to the handle element and the at least one electric contacts to transmit at least one of data and energy,
   wherein the electric connecting device comprises a plurality of portions, wherein a first portion of the pluralities of portions comprises a flexible circuit board in the interior of the handle element and wherein a second portion of the pluralities of portions comprises a rigid circuit board, and wherein the flexible circuit board and the rigid circuit board are electrically and mechanically connected to one another so that the data and/or energy is transmitted by the flexible circuit board and the rigid circuit board.

19. A medical or dental handle element according to claim 18, wherein the rigid circuit board extends transverse to an axis of at least on of: the flexible circuit board, the drive element, the supply line, the longitudinal axis of the handle element.

20. A medical or dental handle element according to claim 18, wherein the rigid circuit board comprises a passage through which at least one of the drive element device, the supply line and a coupling pin of the medical or dental handle element extends.

21. A medical or dental handle element according to claim 18, wherein the flexible circuit board connects to one of the at least one electric contact and terminals to connect to the electric component and the rigid circuit board connects to the other of the at least one electric contact and terminals to connect to the electric component.

* * * * *